(12) United States Patent
Perera et al.

(10) Patent No.: US 9,745,326 B2
(45) Date of Patent: Aug. 29, 2017

(54) BRIDGED ALKALINE EARTH METAL ALKYLPHENATES

(71) Applicant: The Lubrizol Corporation, Wickliffe, OH (US)

(72) Inventors: Jayasooriya Sujith Perera, Twinsburg, OH (US); Gary M. Walker, Allestree (GB); Christopher J. Ciolli, Perry, OH (US); Christopher L. Friend, Willoughby, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 152 days.

(21) Appl. No.: 14/175,164

(22) Filed: Feb. 7, 2014

(65) Prior Publication Data

US 2014/0228266 A1    Aug. 14, 2014

Related U.S. Application Data

(60) Provisional application No. 61/763,037, filed on Feb. 11, 2013.

(51) Int. Cl.
| | | |
|---|---|---|
| *C10M 135/10* | (2006.01) |
| *C07F 3/00* | (2006.01) |
| *C07C 39/15* | (2006.01) |
| *C10M 135/30* | (2006.01) |
| *C10M 159/22* | (2006.01) |
| *C10M 129/14* | (2006.01) |

(52) U.S. Cl.
CPC .............. *C07F 3/003* (2013.01); *C07C 39/15* (2013.01); *C10M 129/14* (2013.01); *C10M 135/30* (2013.01); *C10M 159/22* (2013.01); *C10M 2207/024* (2013.01); *C10M 2207/028* (2013.01); *C10M 2219/087* (2013.01); *C10M 2219/089* (2013.01); *C10N 2230/04* (2013.01); *C10N 2230/08* (2013.01); *C10N 2230/52* (2013.01)

(58) Field of Classification Search
None
See application file for complete search history.

(56) References Cited

U.S. PATENT DOCUMENTS

| | | | |
|---|---|---|---|
| 2,680,096 A | 6/1954 | Walker et al. |
| 3,330,873 A | 7/1967 | Godin et al. |
| 3,464,970 A | 9/1969 | Sakai et al. |
| 3,966,621 A * | 6/1976 | Watkins | C10M 159/22 508/574 |
| 3,992,307 A * | 11/1976 | Hotten | C10M 141/10 252/400.21 |
| 3,992,308 A | 11/1976 | Malec et al. |
| 4,221,673 A | 9/1980 | Robson et al. |
| 4,957,642 A * | 9/1990 | Cleverley | C07C 37/66 508/572 |
| 5,322,529 A * | 6/1994 | Buckley, III | C07C 271/20 44/387 |
| 5,602,084 A * | 2/1997 | Moreton | C10M 159/20 508/391 |
| 5,840,672 A | 11/1998 | Gatto et al. |
| 6,310,009 B1 | 10/2001 | Carrick et al. |
| 6,610,637 B2 | 8/2003 | Curtis et al. |
| 7,435,709 B2 | 10/2008 | Stonebraker et al. |
| 8,198,225 B2 | 6/2012 | Harrison et al. |
| 9,249,091 B2 | 2/2016 | Gibbs et al. |
| 2009/0143264 A1* | 6/2009 | Harrison | C08G 8/28 508/572 |

FOREIGN PATENT DOCUMENTS

| | | |
|---|---|---|
| WO | 98/16597 A1 | 4/1998 |
| WO | 2013059173 A1 | 4/2013 |
| WO | 2013119623 A1 | 8/2013 |

OTHER PUBLICATIONS

N. A. Mukmeneva et al., "New Stabilizers for Butyl Rubber," Russian Journal of Applied Chemistry, Vo. 70 No. 11, pp. 1839-1840, 1997.

* cited by examiner

*Primary Examiner* — Rosalynd Keys
(74) *Attorney, Agent, or Firm* — Christopher D. Hilker; David M. Shold

(57) ABSTRACT

A bridged alkaline earth metal alkylphenate having reduced monomeric alkylphenol is prepared by reacting (a) a 4-alkylphenol, unsubstituted at the ortho positions, (b) an alkaline earth metal oxide or hydroxide, (c) a bridging agent comprising sulfur or a carbonyl compound of 1 to about 6, or to 4 or to 2, carbon atoms, and (d) a 2,6-dialkylphenol. The amount of the 2,6-dialkylphenol is 0.05 to 3 moles per 1 mole of the 4-alkylphenol; if there is a molar excess of the 2,6-dialkylphenol, then the excess is added after initial reaction.

16 Claims, No Drawings

BRIDGED ALKALINE EARTH METAL ALKYLPHENATES

BACKGROUND OF THE INVENTION

The disclosed technology relates to a process for preparing a bridged alkaline earth metal alkylphenate such as dodecylphenate containing a reduced amount of monomeric alkylphenol.

Phenol-based detergents are known. Among these are phenates based on phenolic monomers, linked with sulfur bridges or alkylene bridges such as methylene linkages derived from formaldehyde. The phenolic monomers themselves are typically substituted with an aliphatic hydrocarbyl group to provide a measure of oil solubility. The hydrocarbyl groups may be alkyl groups: historically, dodecylphenol (or propylene tetramer-substituted phenol) has been widely used. An early reference to basic sulfurized polyvalent metal phenates is U.S. Pat. No. 2,680,096, Walker et al., Jun. 1, 1954.

Recently, however, certain alkylphenols and products prepared from them have come under increased scrutiny due to their association as potential endocrine disruptive materials. In particular, alkylphenol detergents which are based on oligomers of C12 alkyl phenols may contain residual monomeric C12 alkyl phenol species. There is interest, therefore, in developing alkyl-substituted phenate detergents, for uses in lubricants, fuels, and as industrial additives, which contain a reduced amount of monomeric dodecylphenol component.

There have been several efforts to prepare phenate detergents that do not contain C12 alkyl phenols or contain reduced amounts of such materials. In some cases these efforts have involved avoiding or minimizing the presence of C12 alkylphenol as a reactant. For instance, U.S. Pat. No. 7,435,709, Stonebraker et al., Oct. 14, 2008, discloses a linear alkylphenol-derived detergent substantially free of endocrine disruptive chemicals. It comprises a salt of a reaction product of (1) an olefin having at least 10 carbon atoms, where greater than 90 mole % of the olefin is a linear C20-C30 n-alpha olefin, and wherein less than 10 mole % of the olefin is a linear olefin of less than 20 carbon atoms, and less than 5 mole % of the olefin a branched chain olefin of 18 carbons or less, and (2) a hydroxyaromatic compound.

U.S. Pat. No. 3,464,970, Sakai et al., Sep. 2, 1969, discloses a process for preparing overbased sulfurized calcium phenates. In an example, an alkylphenol mixture was reacted with calcium oxide and elemental sulfur. In the alkylphenol mixture, those having C4 radicals were 6 mole percent, those having C8 radicals were 18 mole percent, and those having C12 radicals were 76 mole percent. Of the alkylphenols having C8 alkyl radicals, about 36 mole percent was mono-octyl phenol and about 64 percent was di-octylphenol.

U.S. Pat. No. 6,610,637, Curtis et al., Aug. 26, 2003, discloses sulfur-free functionalized alkyl phenol detergents. The functionalization may be an additional hydrocarbyl group such as (among others listed) t-butyl groups.

U.S. Pat. No. 5,840,672, Gatto, Nov. 24, 1998, discloses sulfurized hindered phenols as antioxidants.

U.S. Pat. No. 6,310,009, Carrick et al., Oct. 30, 2001, discloses a saligenin derivative such as the magnesium salt represented by the formula

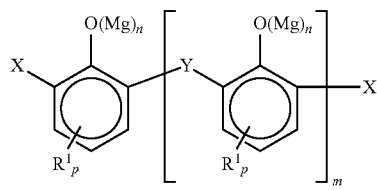

an additive for a lubricating composition. Preferably X is —CHO or —CH$_2$OH, and Y is —CH$_2$— or —CH$_2$OCH$_2$—. R is a hydrocarbyl group containing 1 to 60 carbon atoms and m is 0 to 10.

U.S. Pat. No. 3,992,308, Malec et al., Nov. 16, 1976, discloses a lubricating oil composition containing a sulfurized reaction product of mixed tertiary alkyl phenols with formaldehyde. When used in lubricating oil, they impart improved wear and corrosion inhibiting properties in addition to being effective antioxidants. In an example, 75 weight percent of 2,5-di-tert-butylphenol, 15 weight percent ortho-tertiary butylphenol, and 10 weight percent of 2,4,6-tri-tert-butylphenol was reacted with paraformaldehyde.

U.S. Pat. No. 4,221,673, Robson et al., Sep. 9, 1980, discloses overbased metal phenates prepared by reacting a basic metallic compound with a mixture of an alkyl phenol and an alkydihdroxybenzene. The phenolic composition may comprise certain sulphurised alkyl phenols. An R group substituent is a hydrocarbyl or substituted hydrocarbyl group containing up to 60 carbon atoms. In examples, compositions are prepared from dodecyl phenol and nonyl catechol.

The disclosed technology provides a method for preparing phenate detergent which contains a reduced amount of monomeric dodecylphenol within an oligomeric dodecylphenol composition or, more generally, a reduced amount of monomeric alkylphenol in an oligomeric alkylphenol composition. In certain embodiments such detergents will also exhibit improved antioxidant properties.

SUMMARY OF THE INVENTION

The disclosed technology provides a process for preparing a bridged alkaline earth metal alkylphenate, comprising reacting: (a) a 4-alkylphenol, unsubstituted at the ortho positions, (b) an alkaline earth metal oxide or hydroxide, (c) a bridging agent comprising sulfur or a carbonyl compound of 1 to 6, or to 4 or to 2, carbon atoms, and (d) a 2,6-dialkylphenol; wherein amount of the 2,6-dialkylphenol is 0.05 to 3 moles (or 0.1 to 1.3 or 0.25 to 1.25 moles) per 1 mole of the 4-alkylphenol; provided that if there is a molar excess of the 2,6-dialkylphenol, then such excess is added after initial reaction of the 4-alkylphenol with alkaline earth oxide or hydroxide, the bridging agent, and no more than 1 mole of the 2,6-dialkylphenol per mole of the 4-alkylphenol.

The disclosed technology further provides a bridged alkaline earth metal alkylphenate represented by the formula

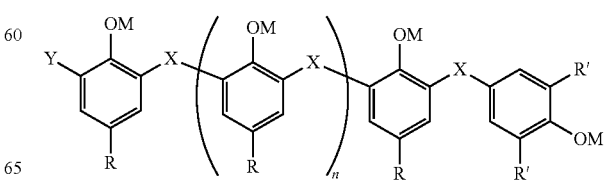

where n is 0 to 8; each M is independently hydrogen or a bond to a metal ion, provided that at least one M represents a bond to an alkaline earth metal ion; each R is independently an alkyl group of 10 to 30 carbon atoms; each R' is independently an alkyl group; X is $S_x$, or an alkylene (that is, a divalent alkyl) group of 1 to 4 carbon atoms, where x is 1 to 4, or 1 to 2, or 1; and Y is H or —SH or a group represented by the formula

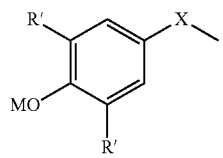

where X, M, and R' are as defined above.

The disclosed technology further provides a lubricant composition comprising an oil of lubricating viscosity and the product described above, as well as a method for lubricating a mechanical device comprising supplying thereto such a lubricant composition.

DETAILED DESCRIPTION OF THE INVENTION

Various preferred features and embodiments will be described below by way of non-limiting illustration.

The process of the present technology involves reacting a specified mixture of alkylphenols with an alkaline earth metal oxide or hydroxide and a bridging agent. The mixture of alkylphenols will include a 4-alkylphenol (also known as a para-alkyl phenol). The 4-alkylphenol will by typically or predominantly unsubstituted at the ortho positions, although this is not to exclude the possibility of a small amount of ortho substitution, on, e.g., up to 10 mole percent or 5 or 2 or 1 or 0.1 mole percent, e.g., 0.1 to 10 mole percent, of the 4-substituted alkylphenols. The free or unsubstituted ortho positions are desirable in order to permit bridging between individual monomer units at those positions, as will be described below; and it is desired that there be two reactive positions free and unsubstituted, to permit formation of oligomeric chains. (The meta, or 3- and 5-positions are not normally particularly reactive toward bridging or linking reactions and are generally discounted.) Thus there may be a mixture of a 4-alkylphenol, often in a major or even a predominant amount, with an optional amount, sometimes a minor amount, of a 2-alkylphenol and/or a minor amount of a 2,4-dialkylphenol, and optionally other isomers. If multiple alkyl groups are present, the alkyl groups may be the same or they may be different. The alkyl group or groups may be linear or non-linear, i.e., branched or containing a cyclic structure. One common alkyl group is derived from propylene tetramer, so that the alkyl group may have branching characteristic of the propylene tetramer.

The alkyl group that is present in the 4-position on the phenol will typically have 8 to 36, or 10 to 30, or to 24, or to 20, or to 18 carbon atoms, or alternatively, 20 to 36 or 22 to 30 or 24 to 28 carbon atoms. In one embodiment, the alkyl group may have 12 to 18 carbon atoms, or mixtures thereof, and in one embodiment it may comprise a C12 alkyl group, that is, a dodecyl group. In that instance, the alkyl phenol may comprise or be para-dodecylphenol, ("PDDP").

If the alkylphenol is PDDP, other substituted phenols may be present as well as the PDDP, but the PDDP will typically comprise at least 50 weight percent of the monomeric phenolic component and may be 50 to 100 weight percent, or 60 to 99% or 70 to 98% or 80 to 97% or 90-96% or 95 to 98%. Typically, a commercial grade of PDDP may be used, such that phenolic components other than PDDP will be those materials that are present along with the PDDP in the commercial grade material. Thus, a certain amount of other isomers may be present, predominantly orthododecylphenol or meta-dodecylphenol, but there may also be an amount of unsubstituted phenol and an amount of unreacted dodecene, as well as a minor amount of dialkylated material. Moreover, since dodecylphenols are typically prepared by the reaction of a propylene tetramer with a phenol, certain amounts of material having C9 or C15 alkyl groups, or a mixture of alkyl groups having 9 (or fewer) to 15 (or more) carbon atoms, may also be present. Some of these may result from reaction with propylene trimer or pentamer. Characteristically, the amount of such other materials may be 5 or 15 to 50 percent or 20 to 40, or 25 to 35, or 35 to 40 percent by weight, in commercial PDDP. The amounts of PDDP referred to herein generally refer to the total amount of the commercial grade, which would include such isomers, byproducts, and other materials.

Also present in addition to the 4-alkylphenol will be a 2,6-dialkylphenol, that is, a phenol with substituents in the two ortho positions but no substituent in the 4- or para position. The two alkyl groups may be the same or different from each other, but they will typically have fewer carbon atoms than the alkyl group present in the 4-position on the 4-alkylphenol, e.g., they may typically have 1 to 10 or 1 to 8 or 2 to 6 or 4 carbon atoms each. A suitable example of such a material is 2,6-di-tert-butylphenol, which is readily available. Other such materials include 2,6-di-sec-butylphenol and 2,6-dimethylphenol. As in the case of the 4-alkylphenol, there may be minor amounts of other isomers present, such as the 2,4-dialkylphenol, and such materials may be present in amount of up to 20 weight percent or up to 10 or 5 or 2 weight percent, e.g., 0.1 to 1 weight percent. The majority of this second alkylphenol will be a disubstituted material which has only one position (typically, para) available for bridging or linking or capping reaction.

The amount of the 2,6-dialkylphenol employed may be 0.05 to 3 moles per 1 mole of the 4-alkylphenol, or 0.1 to 1.25, or 0.15 to 1, or 0.15 to 0.8, or 0.15 to 0.5, or 0.25 to 1.3, or about 0.20, moles per mole. It is possible, therefore, that there may be a modest molar excess of the 2,6-dialkylphenol, e.g., greater than 1 to 1.25 moles thereof per mole of the 4-alkylphenol. If that is the case, then such excess will be is added after initial reaction, as described in greater detail below, of the 4-alkylphenol with alkaline earth oxide or hydroxide, the bridging agent, and no more than 1 mole of the 2,6-dialkylphenol per mole of the 4-alkylphenol.

The 4-alkylphenol and, to the extent it may be present at this stage, the 2,6-dialkyl phenol, are reacted with an alkaline earth metal oxide or hydroxide. The alkaline earth metal oxide or hydroxide, being a basic material, will interact with the acidic phenolic OH group by neutralization to form the alkaline earth metal salt, or by other known interactions. Certain alkaline earth metals include magnesium, calcium, and barium, and in certain embodiments the alkaline earth metal may be magnesium or calcium or mixtures thereof, and in other embodiments it may be calcium. A suitable material is calcium hydroxide.

The amount of the alkaline earth metal oxide or hydroxide employed at this stage of the preparation will typically be 0.1 to 0.5 moles (that is, 0.2 to 1 equivalents) per mole of the 4-alkylphenol. Other amounts may be 0.15 to 0.45 or 0.2 to 0.35 moles per mole. Additional oxide or hydroxide may be supplied in a subsequent optional overbasing step.

The 4-alkylphenol (and optionally 2,6-dialkylphenol) may be reacted with the alkaline earth metal oxide or hydroxide in the presence a solvent. In one embodiment, a relatively small amount of a solvent such as ethylene glycol may be used, which may serve to facilitate the reaction and, indeed, be present throughout the steps of the reaction until it is optionally removed from the final product. The amount of the solvent may be 0.1 to 100 percent of the 4-alkylphenol on a weight basis, or 1 to 10 percent or 1.5 to 5 percent or 2 to 4 percent.

The initial mixing or reaction may be conducted at an elevated temperature of 50 to 200° C. or 80-150° C. or 90-120° C. The result of the initial mixing or reacting will be a partially or completely neutralized salt or interaction product of the 4-alkylphenol (and optionally 2,6-dialkylphenol) with the alkaline earth metal.

The reaction mixture will also be reacted with a bridging agent to link together units of the 4-alkylphenol at one or more ortho positions. In one embodiment the bridging agent may be sulfur. The use of sulfur to create bridges between phenolic monomers is well known and need not be described in great detail. Briefly, a source of sulfur such as elemental sulfur is added to the 4-alkylphenol (and, if present initially, the 2,6-dialkylphenol). The addition may occur simultaneously with the addition of the alkaline earth metal oxide or hydroxide, or it may occur after the initial addition of the oxide or hydroxide. The amount of sulfur may be 0.8 to 4 moles of sulfur per 1 mole of the 4-alkylphenol, or 1 to 3 or 1.5 to 2.5 or 1.7 to 2 or 1.3 to 3 or 1.7 to 3 moles S per mole. For purposes of this document, 1 mole of sulfur is considered to be 32 g, referring to one mole of S atoms ($S_1$) regardless of the bonded structure of the elemental sulfur.

The reaction with sulfur to provide the sulfur bridged material will typically be conducted at an elevated temperature such as 150 to 230° C., or 180 to 225° C. or 200 to 220° C. or 215 to 220° C. The reaction time will depend on the temperature, as is known to those skilled in the art, and may include 1 to 15 hours, or 2 to 10, or 3 to 8, or 4 to 6 hours.

Alternatively, the bridging agent may be a carbonyl compound of 1 to 6 carbon atoms, or 1 to 4, or 1 to 2, or 1 carbon atom. This may be an aldehyde or ketone, and may typically be an aldehyde or reactive equivalent thereof such as formaldehyde (or formalin or paraformaldehyde). The carbonyl compound will be reacted to form an alkylene linkage. Formaldehyde, for instance, will typically form a —$CH_2$— linking group; acetaldehyde will form a —$C(CH_3)$H— linking group. To effect linkage with a methylene group, two moles (or 1.5 to 2.5 moles) of formaldehyde may be reacted per 1 mole of 4-alkylphenol in the presence of base catalyst at 30-55° C. (or 35-53° C.) for a short period of time such as 5 minutes, in the presence of a diluent such as oil. Thereafter, metal oxide may be added in one or more portions as the temperature is increased through 75-85° C. and up to 90-120° C. or 95-100° C. and holding at that temperature for a suitable period of time such as ½ to 2 hours, or about 1 hour. If desired, diluent oil may be added, volatiles may be removed by vacuum stripping at elevated temperature, and the material may be filtered to remove solids.

As has been mentioned earlier, the 2,6-dialkylphenol may be included with the 4-alkylphenol at the start of the reaction, that is, at the time of the initial reaction with the alkaline earth metal oxide or hydroxide and the bridging agent. Alternatively, some of the 2,6-material may be present initially and some may be added after the initial reaction with the alkaline earth metal oxide or hydroxide and the bridging agent. As another alternative, the 2,6-material may be added after the initial mixing and reaction of the other material, after the initial reaction has progressed toward completion or is substantially complete. In some instances the addition of the 2,6-material after the coupling reaction may be more efficient at reducing the level of residual 4-alkylphenol material in the product. While not wishing to be bound by any theory, it is speculated that the 2,6-dialkylphenol may react more efficiently (under coupling conditions) with monomeric 4-alkylphenol than with oligomers thereof, and thus addition of the 4-alkylphenol after the coupling (oligomerization) reaction has progressed toward completion may lead to more efficient removal of residual 4-alkylphenol. Moreover, it is speculated that terminal units of the 2,6-material may minimize the decomposition of the oligomer to release monomer units of the 4-alkylphenol.

Thus, in one embodiment the 4-alkylphenol is reacted with at least a portion of the alkaline earth metal oxide or hydroxide and at least a portion of the bridging agent prior to addition of the 2,6-dialkylphenol. More specifically, in one embodiment, in a first step, 0.1 to 0.5 or to 0.4 moles (or 0.2 to 0.33 moles) of calcium hydroxide and 1 to 3 moles (or 1.3 to 2.7 moles) of sulfur (as $S_1$), per mole of the 4-alkylphenol, are reacted with the 4-alkylphenol (such as dodecylphenol) at 170 to 230° C. for 3 to 7 hours, optionally in the presence of ethylene glycol (0.1 to 0.3 moles, or 0.1 to 0.15 moles), and thereafter 0.05 to 0.5 moles of additional calcium hydroxide, 0.25 to 0.8 moles (or 0.6 to 0.7 moles) of additional sulfur, and 0.15 to 0.5 (or 0.2 to 0.3) moles of the 2,6-dialkylphenol (such as di-tert-butylphenol), as well as, optionally, additional ethylene glycol (0.02 to 0.1 or 0.04 to 0.06 moles), per mole of the 4-alkylphenol, are added and reacted at 150 to 230° C. for 1 to 5 hours. The reaction mixture may optionally be vacuum stripped to remove volatiles (e.g., 215° C., 1 hour).

In another embodiment, 1 mole of the 4-alkylphenol (relative molar amount) is mixed with 0.15 to 0.5 moles (e.g., 0.25 moles) of di-t-butylphenol and with 0.1 to 0.6 moles (e.g., 0.32 moles) calcium hydroxide, optionally in the presence of ethylene glycol (0.1 to 0.6 moles, e.g., 0.14 or 0.27 moles) and the mixture heated to 110 to 125° C. (e.g. 117° C.). To this mixture is added 1.5 to 2.5 moles (e.g., 1.85 or 2.0 moles) sulfur and the mixture is heated to 200 to 230° C. (e.g., 215° C.) for 4 to 6 hours (e.g., 5 hours). The reaction mixture may optionally be vacuum stripped, as above.

The product of these reactions will be a bridged alkaline earth metal alkylphenate which may be represented by the formula

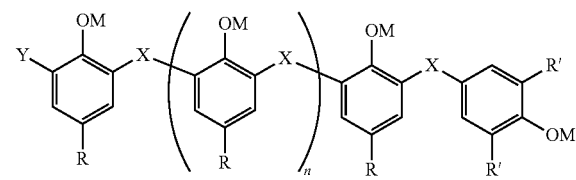

In this formula, n may be 0 to 8, or 1 to 6, or 1 to 4, or 1 to 3, or 2 to 4, or 2; each M is independently hydrogen or a bond to a metal ion, provided that at least one M represents a bond to an alkaline earth metal ion such as calcium; each R is independently an alkyl group of 10 to 30 carbon atoms, or 10 to 24, or 10 to 18, or 12 carbon atoms;

each R' is independently an alkyl group, having typically 1 to 8 carbon atoms such as 2 to 6 or 4, and typically being a branched alkyl group such as a t-butyl group. X is $S_x$ (that is a sulfur atom or a sulfur chain) where x is 1 to 4, or 1 to 2, or 1, or an alkylene (that is, a divalent alkyl) group of 1 to 4 carbon atoms, typically a methylene group. Y is H or —SH or a group represented by the formula

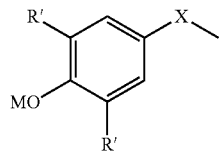

where X, M, and R' are as previously defined. (The short line emanating from the X represents a bond or point of attachment.)

The oligomeric product as described above may be, further, overbased. That is, it may be subsequently treated with a molar excess of a base such as an alkaline earth metal oxide or hydroxide and with an acidic gas such as carbon dioxide, thereby providing an overbased detergent.

Overbased detergents are overbased materials, otherwise referred to as overbased or superbased salts, which are generally homogeneous Newtonian systems having by a metal content in excess of that which would be present for neutralization according to the stoichiometry of the metal and the detergent anion. The amount of excess metal is commonly expressed in terms of metal ratio, that is, the ratio of the total equivalents of the metal to the equivalents of the acidic organic compound. The overbased materials are prepared by reacting an acidic material (typically an inorganic acid or lower carboxylic acid, in one embodiment, carbon dioxide) with a mixture comprising an acidic organic compound, a reaction medium comprising at least one inert, organic solvent (e.g., mineral oil, naphtha, toluene, xylene) for said acidic organic material, a stoichiometric excess of a metal base, and a promoter such as a phenol or alcohol and optionally ammonia. The acidic organic material, in the case of the materials of the disclosed technology, will be the oligomeric bridged phenolic material described herein. The amount of excess metal is commonly expressed in terms of metal ratio. The term "metal ratio" is the ratio of the total equivalents of the metal to the equivalents of the acidic organic compound. A neutral metal salt has a metal ratio of one. A salt having 4.5 times as much metal as present in a normal salt will have metal excess of 3.5 equivalents, or a ratio of 4.5.

Overbased detergents may be characterized by Total Base Number (TBN), the amount of strong acid needed to neutralize all of the material's basicity, expressed as mg KOH per gram of sample. Since overbased detergents are commonly provided in a form which contains diluent oil, for the purpose of this document, TBN is to be recalculated to an oil-free basis. Some useful detergents may have a TBN of 100 to 800, or 150 to 750, or, 400 to 700.

The metal compounds useful in making the basic metal salts are generally any Group 1 or Group 2 metal compounds (CAS version of the Periodic Table of the Elements). Examples include alkali metals such as sodium, potassium, lithium, copper, magnesium, calcium, barium, zinc, and cadmium. In one embodiment the metals are sodium, magnesium, or calcium. The anionic portion of the salt can be hydroxide, oxide, carbonate, borate, or nitrate. In certain embodiments the metal compound will be calcium oxide or calcium hydroxide.

Overbased materials are well known to those skilled in the art. Patents describing techniques for making basic salts of sulfonic acids, carboxylic acids, (hydrocarbyl-substituted) phenols, phosphonic acids, and mixtures of any two or more of these include U.S. Pat. Nos. 2,501,731; 2,616,905; 2,616,911; 2,616,925; 2,777,874; 3,256,186; 3,384,585; 3,365,396; 3,320,162; 3,318,809; 3,488,284; and 3,629,109.

The product of the disclosed technology may be subjected to vacuum stripping or other known techniques for removal of volatile materials such as water or hydrogen sulfide. This removal may be applied to the mixture of the bridged oligomeric phenolic compound prior to or after any overbasing procedure.

The product of the disclosed technology may beneficially be used as an additive in a lubricant. The amount of the bridged oligomeric phenolic compound in a lubricant may be 0.1 to 8 percent by weight, on an oil-free basis, but including the calcium carbonate and other salts present in an overbased composition. When present as an overbased detergent, the amount may typically be in the range of 0.1 to 25 weight percent, or 0.2 to 28, or 0.3 to 20, or 0.5 to 15 percent. The higher amounts are typical of marine diesel cylinder lubricants, e.g., 1 or 3 or 5 percent up to 25, 20, or 15 percent. Amounts used in gasoline or heavy-duty diesel engines (not marine) will typically be in lower ranges, such as 0.1 to 10 percent or 0.5 to 5 or 1 to 3 percent by weight. When used as a substantially neutral or non-overbased salt, its amount may typically be correspondingly less for each of the engine types, e.g., 0.1 to 10 percent or 0.2 to 8 or 0.3 to 6 percent.

A major constituent of a lubricant will typically be an oil of lubricating viscosity, also referred to as a base oil. The base oil may be selected from any of the base oils in Groups I-V of the American Petroleum Institute (API) Base Oil Interchangeability Guidelines, namely

| Base Oil Category | Sulfur (%) | | Saturates (%) | Viscosity Index |
|---|---|---|---|---|
| Group I | >0.03 | and/or | <90 | 80 to 120 |
| Group II | ≤0.03 | and | ≥90 | 80 to 120 |
| Group III | ≤0.03 | and | ≥90 | >120 |
| Group IV | All polyalphaolefins (PAOs) | | | |
| Group V | All others not included in Groups I, II, III or IV | | | |

Groups I, II and III are mineral oil base stocks. The oil of lubricating viscosity can include natural or synthetic oils and mixtures thereof. Mixture of mineral oil and synthetic oils, e.g., polyalphaolefin oils and/or polyester oils, may be used.

Natural oils include animal oils and vegetable oils (e.g. vegetable acid esters) as well as mineral lubricating oils such as liquid petroleum oils and solvent-treated or acid treated mineral lubricating oils of the paraffinic, naphthenic, or mixed paraffinic-naphthenic types. Hydrotreated or hydrocracked oils are also useful oils of lubricating viscosity. Oils of lubricating viscosity derived from coal or shale are also useful.

Synthetic oils include hydrocarbon oils and halosubstituted hydrocarbon oils such as polymerized and interpolymerized olefins and mixtures thereof, alkylbenzenes, polyphenyl, alkylated diphenyl ethers, and alkylated diphenyl sulfides and their derivatives, analogs and homologues thereof. Alkylene oxide polymers and interpolymers and derivatives thereof, and those where terminal hydroxyl groups have been modified by, e.g., esterification or etherification, are other classes of synthetic lubricating oils. Other suitable synthetic lubricating oils comprise esters of dicarboxylic acids and those made from C5 to C12 monocarboxylic acids and polyols or polyol ethers. Other synthetic lubricating oils include liquid esters of phosphorus-containing acids, polymeric tetrahydrofurans, silicon-based oils such as poly-alkyl-, polyaryl-, polyalkoxy-, or polyaryloxy-siloxane oils, and silicate oils.

Other synthetic oils include those produced by Fischer-Tropsch reactions, typically hydroisomerized Fischer-Tropsch hydrocarbons or waxes. In one embodiment oils may be prepared by a Fischer-Tropsch gas-to-liquid synthetic procedure as well as other gas-to-liquid oils.

Unrefined, refined, and rerefined oils, either natural or synthetic (as well as mixtures thereof) of the types disclosed hereinabove can used. Unrefined oils are those obtained directly from a natural or synthetic source without further purification treatment. Refined oils are similar to the unrefined oils except they have been further treated in one or more purification steps to improve one or more properties. Rerefined oils are obtained by processes similar to those used to obtain refined oils applied to refined oils which have been already used in service. Rerefined oils often are additionally processed to remove spent additives and oil breakdown products.

Additional conventional components may be used in preparing a lubricant according to the present invention, for instance, those additives typically employed in a crankcase lubricant. Crankcase lubricants may typically contain any or all of the following components hereinafter described.

One such additive is a detergent, in addition to the bridged phenolic compound of the disclosed technology. Detergents have been described in a general way above. Most conventional detergents used in the field of engine lubrication, provide basicity or TBN to the lubricant, due to the presence of basic metal compounds (metal hydroxides, oxides, or carbonates, typically based on such metals as calcium, magnesium, or sodium). Such metallic overbased detergents, also referred to as overbased or superbased salts, are generally single phase, homogeneous Newtonian systems characterized by a metal content in excess of that which would be present for neutralization according to the stoichiometry of the metal and the particular acidic organic compound reacted with the metal. The overbased materials are typically prepared by reacting an acidic material (typically an inorganic acid or lower carboxylic acid such as carbon dioxide) with a mixture of an acidic organic compound (also referred to as a substrate), a stoichiometric excess of a metal base, typically in a reaction medium of an one inert, organic solvent (e.g., mineral oil, naphtha, toluene, xylene) for the acidic organic substrate. Optionally a small amount of promoter such as a phenol or alcohol is present. The acidic organic substrate will normally have a sufficient number of carbon atoms to provide a degree of solubility in oil.

Such conventional overbased materials and their methods or preparation are well known to those skilled in the art. Patents describing techniques for making basic metallic salts of sulfonic acids, carboxylic acids, phenols, phosphonic acids, and mixtures of any two or more of these include U.S. Pat. Nos. 2,501,731; 2,616,905; 2,616,911; 2,616,925; 2,777,874; 3,256,186; 3,384,585; 3,365,396; 3,320,162; 3,318,809; 3,488,284; and 3,629,109. Salixarate detergents are described in U.S. Pat. No. 6,200,936 and PCT Publication WO 01/56968. Saligenin detergents are described in U.S. Pat. No. 6,310,009.

The amount of such an additional or supplemental detergent, if present in a lubricant, may be 0.1 to 8, or 0.2 to 7, or 0.5 to 6 or 1 to 3 weight percent.

Another additive is a dispersant. Dispersants are well known in the field of lubricants and include primarily what is known as ashless-type dispersants and polymeric dispersants. Ashless type dispersants are characterized by a polar group attached to a relatively high molecular weight hydrocarbon chain. Typical ashless dispersants include nitrogen-containing dispersants such as N-substituted long chain alkenyl succinimides, also known as succinimide dispersants. Succinimide dispersants are more fully described in U.S. Pat. Nos. 4,234,435 and 3,172,892. Another class of ashless dispersant is high molecular weight esters, prepared by reaction of a hydrocarbyl acylating agent and a polyhydric aliphatic alcohol such as glycerol, pentaerythritol, or sorbitol. Such materials are described in more detail in U.S. Pat. No. 3,381,022. Another class of ashless dispersant is Mannich bases. These are materials which are formed by the condensation of a higher molecular weight, alkyl substituted phenol, an alkylene polyamine, and an aldehyde such as formaldehyde and are described in more detail in U.S. Pat. No. 3,634,515. Other dispersants include polymeric dispersant additives, which are generally hydrocarbon-based polymers which contain polar functionality to impart dispersancy characteristics to the polymer. Dispersants can also be post-treated by reaction with any of a variety of agents. Among these are urea, thiourea, dimercaptothiadiazoles, carbon disulfide, aldehydes, ketones, carboxylic acids, hydrocarbon-substituted succinic anhydrides, nitriles, epoxides, boron compounds, and phosphorus compounds. References detailing such treatment are listed in U.S. Pat. No. 4,654,403. The amount of dispersant in the present composition can typically be 1 to 10 weight percent, or 1.5 to 9.0 percent, or 2.0 to 8.0 percent, all expressed on an oil-free basis.

Another component is an antioxidant. Antioxidants encompass phenolic antioxidants, which may comprise a butyl substituted phenol containing 2 or 3 t-butyl groups. The para position may also be occupied by a hydrocarbyl group, an estercontaining group, or a group bridging two aromatic rings. Antioxidants also include aromatic amine, such as nonylated diphenylamines or alkylated phenylnaphthylamine. Other antioxidants include sulfurized olefins, titanium compounds, and molybdenum compounds. U.S. Pat. No. 4,285,822, for instance, discloses lubricating oil compositions containing a molybdenum and sulfur containing composition. U.S. Patent Application Publication 2006-0217271 discloses a variety of titanium compounds, including titanium alkoxides and titanated dispersants, which materials may also impart improvements in deposit control and filterability. Other titanium compounds include titanium carboxylates such as neodecanoate. Typical amounts of antioxidants will, of course, depend on the specific antioxidant and its individual effectiveness, but illustrative total amounts can be 0.01 to 5 percent by weight or 0.15 to 4.5 percent or 0.2 to 4 percent. Additionally, more than one antioxidant may be present, and certain combinations of these can be synergistic in their combined overall effect.

Viscosity improvers (also sometimes referred to as viscosity index improvers or viscosity modifiers) may be included in the compositions of this invention. Viscosity improvers are usually polymers, including polyisobutenes, polymethacrylic acid esters, diene polymers, polyalkylstyrenes, esterified styrene-maleic anhydride copolymers, alkenylarene-conjugated diene copolymers and polyolefins. Multifunctional viscosity improvers, which also have dispersant and/or antioxidancy properties are known and may optionally be used. The amount of a viscosity improver, if present, may typically be 0.1 to 5, or 0.2 to 4, or 0.3 to 3, or 0.5 to 2 weight percent (oil free basis) although higher amounts, e.g., up to 10 percent or higher, may be used in certain applications.

Another additive is an antiwear agent. Examples of antiwear agents include phosphorus-containing antiwear/extreme pressure agents such as metal thiophosphates, phosphoric acid esters and salts thereof, phosphorus-containing carboxylic acids, esters, ethers, and amides; and phosphites. In certain embodiments a phosphorus antiwear agent may be present in an amount to deliver 0.01 to 0.2 or 0.015 to 0.15 or 0.02 to 0.1 or 0.025 to 0.08 percent phosphorus. Often the antiwear agent is a zinc dialkyldithiophosphate (ZDP). For a typical ZDP, which may contain 11 percent P (calculated on an oil free basis), suitable amounts may include 0.09 to 0.82 percent. Non-phosphorus-containing anti-wear agents include borate esters (including borated epoxides), dithiocarbamate compounds, molybdenum-containing compounds, and sulfurized olefins.

Other materials that may be used as antiwear agents include tartrate esters, tartramides, and tartrimides. Examples include oleyl tartrimide (the imide formed from oleylamine and tartaric acid) and oleyl diesters (from, e.g., mixed C12-16 alcohols). Other related materials that may be useful include esters, amides, and imides of other hydroxycarboxylic acids in general, including hydroxy-polycarboxylic acids, for instance, acids such as tartaric acid, citric acid, lactic acid, glycolic acid, hydroxy-propionic acid, hydroxy-glutaric acid, and mixtures thereof. These materials may also impart additional functionality to a lubricant beyond antiwear performance. These materials are described in greater detail in US Publication 2006-0079413 and PCT publication WO2010/077630. Such derivatives of (or compounds derived from) a hydroxy-carboxylic acid, if present, may typically be present in the lubricating composition in an amount of 0.1 weight % to 5 weight %, or 0.2 weight % to 3 weight %, or greater than 0.2 weight % to 3 weight %.

Other additives that may optionally be used in lubricating oils include pour point depressing agents, extreme pressure agents, anti-wear agents, color stabilizers, and anti-foam agents.

Other materials that may be present and may provide one or more of antioxidancy, antiwear performance, deposit control, and improved filterability include titanium compounds such as titanium alkoxides (e.g. titanium isopropoxide, titanium 2-ethylhexoxide), titanium modified dispersants, and titanium carboxylates such as titanium neodecanoate. Titanium compounds and methods for their preparation are disclosed in WO2006/105022. Other metal compounds include molybdenum compounds such as molybdenum dithiocarbamates.

The lubricant herein described may be uses for lubricating a mechanical device, which will comprise supplying thereto the lubricant composition as described herein. In certain embodiments the mechanical device comprises an internal combustion engine. It may also be used in driveline applications such as lubricants designed for an automatic transmission, a manual transmission, a continuously variable transmission, a wet clutch, a dual clutch transmission, a synchronizer, or a gear.

Typical or suitable engines include gasoline or spark-ignited engines such as passenger car engines, diesel or compression-ignited engines such as passenger car diesel engines heavy duty diesel truck engines, natural gas fueled engines such as stationary power engines, alcohol-fueled engines, mixed gasoline/alcohol fueled engines, bio-diesel fueled engines, hydrogen-fueled engines, two-cycle engines, aviation piston or turbine engines, and marine or railroad diesel engines. In one embodiment the internal combustion engine may be a diesel fueled engine and in another embodiment a gasoline fueled engine. The internal combustion engine may be fitted with an emission control system or a turbocharger. Examples of emission control systems include diesel particulate filters (DPF) and systems employing selective catalytic reduction (SCR).

The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, byproducts, derivatives, and other such materials which are normally understood to be present in the commercial grade.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include: hydrocarbon substituents, including aliphatic, alicyclic, and aromatic substituents; substituted hydrocarbon substituents, that is, substituents containing non-hydrocarbon groups which, in the context of this invention, do not alter the predominantly hydrocarbon nature of the substituent; and hetero substituents, that is, substituents which similarly have a predominantly hydrocarbon character but contain other than carbon in a ring or chain. A more detailed definition of the term "hydrocarbyl substituent" or "hydrocarbyl group" is found in paragraphs [0137] to [0141] of published application US 2010-0197536.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

EXAMPLES

Example 1

PDDP with DTBP Up-Front Addition

Part A. 504 g of para-dodecylphenol (PDDP, from propylene tetramer) is mixed with 98.27 g 2,6-di-t-butylphenol (DTBP) in a 3-L, four-necked round-bottom flask, equipped with a thermowell, nitrogen inlet with subsurface sparge tube, a Dean-Stark trap, a Friedrichs condenser, and a sodium hydroxide/bleach scrubber. The mixture is heated with stirring to 105° C. To the mixture are charged 44.4 g calcium hydroxide and 16.8 g ethylene glycol, and the mixture is heated to 117° C. At this point 122.4 g of elemental sulfur is added. The reaction mixture is heated to 215° C. under nitrogen flow (14 (0.5 ft$^3$) per hour) and maintained at this temperature for 5 hours. At the end of this reaction time, while still at temperature, the mixture is subjected to vacuum (pressure about 5-6 kPa (40-45 torr)) for 1 hour to remove volatiles, including removal of some of the unreacted monomers. 122.8 g diluent oil is added and the mixture is allowed to cool to room temperature.

Part B. The total amount of material from Part A is heated to 100° C. under nitrogen flow (14 L/hr). To this material is added 177 g decanol, 150 g ethylene glycol, and 42.2 g of an alkylbenzenesulfonic acid. After standing at room temperature overnight (under nitrogen flow), the material is reheated to 100° C. and 218 g calcium hydroxide is added. The mixture is heated to 165° C. and blown with carbon dioxide at a rate of 14 to 17 L/hour (0.5 to 0.6 ft$^3$/hr) for 2.35 hours. The reaction is vacuum stripped at about 5-6 kPa (40-45 torr) for 1 hour at 216° C. 75.5 g polyisobutenyl succinic anhydride and 470 g diluent oil are added, and the mixture is filtered using filter aid. The filtrate (including about 37.4% diluent oil) is the overbased detergent. It has a TBN (oil-containing) of 232 (by potentiometric titration).

Analysis of the material of Part B by ultraperformance liquid chromatography indicates the presence of 3.08 percent free PDDP (including sulfurized PDDP monomer). This represents a reduction from the 5.15 percent present in a baseline material made by without the addition of the DTBP at the same dilution.

Part C. 5.0 weight percent of the product of Part B is added to 95 parts by weight of 150 N mineral oil, to duplicate the concentration of the overbased detergent of Part B in a typical lubricant formulation. The mixture is subjected to a Panel Coker test in which the oil sample is splashed onto a metal panel held at 325° C. in a cycle of splashing and baking for 3.5 hours. The panel receives an image of 83%, where 100% indicates no deposits and 0 indicates heavy black varnish. The baseline material (prepared without the DTBP) shows a similar rating of 78%, indicating that there is no adverse effect from use of the DTBP.

The formulation of Part C is also subjected to an oxidative stability test (rotating pressure vessel oxidation time (RPBOT), ASTM D2272—higher values indicated greater oxidation resistance). The test exhibits a value of 221 minutes, which outperforms the baseline material (without the DTBP) at 160 minutes.

Example 2

PDDP with Intermediate Addition of DTBP

Part A. 501.4 g of para-dodecylphenol (PDDP, from propylene tetramer) is heated to 105° C. with stirring in a 3-L, four-necked round-bottom flask, equipped with a thermowell, nitrogen inlet with subsurface sparge tube, a Dean-Stark trap, a Friedrichs condenser, and a sodium hydroxide/bleach scrubber. To the PDDP are charged 29.7 g calcium hydroxide and 11.14 g ethylene glycol, and the mixture is heated to 117° C. At this point 122.6 g of elemental sulfur is added. The reaction mixture is heated to 215° C. under nitrogen flow (14 L/hr) and maintained at this temperature for 4 hours. At this point there are charged an additional 14.7 g calcium hydroxide, 6.01 g ethylene glycol, 40.8 g elemental sulfur, and 98.08 g di-t-butyl phenol (DTBP). The mixture is maintained at 215° C. for an additional 2 hours. The reaction mixture is vacuum stripped and diluted with 122.8 g diluent oil as in Example 1.

Part B. The material from Part A is overbased as in Example 1, except that the amount of decanol is 175.2 g, the amount of ethylene glycol is 148.2 g, the amount alkylbenzenesulfonic acid is 43 g, and the amount of calcium hydroxide is 218 g, and without the overnight cool-down. Carbon dioxide is blown for 2.45 hours; the amount of diluent oil added is 469.5 g and the amount of polyisobutenyl succinic anhydride is 73.6 g. The filtrate (including about 36% diluent oil) is the overbased detergent. It has a TBN (oil-containing) of 235.

Analysis of the material of Part B by ultraperformance liquid chromatography indicates the presence of 2.25 percent free PDDP (including sulfurized PDDP monomer). This represents a further reduction in the amount of PDDP.

Part C. 5.0 weight percent of the product of Part B is added to 95 parts by weight of 150 N mineral oil and tested as in Example 1 The panel receives a Panel Coker image rating of 72%, again indicating no significant adverse effect from use of the DTBP.

The formulation of Part C is also subjected to the RPBOT test. The material exhibits a value of 242 minutes, which again outperforms the baseline material.

Example 3

Product from C24-28 Alkyl Phenol

Example 1 is substantially repeated except that the 504 g PDDP is replaced by 870.74 g C24-28 alkyl phenol which contains a significant fraction of 4-substituted material. In part B, the amount of decanol is 174.63 g, the amount of ethylene glycol is 149.35 g, the amount of alkylbenzenesulfonic acid is 42.6 g, the amount of calcium hydroxide is 219.2 g, and carbon dioxide is blown for 2.35 hours. After vacuum stripping, 74.92 g polyisobutenyl succinic anhydride and 468.34 g of diluent oil are added. A formulation prepared as in Part C of Example 1 exhibits a Panel Coker rating of 81% and an RPVOT result of 222 minutes.

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements. As used herein, the term "comprising" is intended also to encompass as alternative embodiments "consisting essentially of" and "consisting of." "Consisting essentially of" permits the inclusion of substances that do not materially affect the basic and novel characteristics of the composition under consideration.

What is claimed is:

1. A process for preparing a bridged alkaline earth metal alkylphenate, comprising reacting:
    (a) a 4-alkylphenol, unsubstituted at the ortho positions,
    (b) an alkaline earth metal oxide or hydroxide,
    (c) a bridging agent comprising sulfur or a carbonyl compound of 1 to about 6 carbon atoms, and
    (d) a 2,6-dialkylphenol;
wherein amount of the 2,6-dialkylphenol is about 0.05 to about 3 moles per 1 mole of the 4-alkylphenol; provided that if there is a molar excess of the 2,6-dialkylphenol, then such excess is added after initial reaction of the 4-alkylphenol with alkaline earth oxide or hydroxide, the bridging agent, and no more than 1 mole of the 2,6-dialkylphenol per mole of the 4-alkylphenol.

2. The process of claim 1 wherein the 4-alkylphenol is 4-dodecylphenol.

3. The process of claim 1 wherein the alkaline earth metal oxide or hydroxide is calcium hydroxide.

4. The process of claim 1 wherein the bridging agent is formaldehyde.

5. The process of claim 1 wherein the bridging agent is sulfur.

6. The process of claim 1 wherein the 2,6-dialkylphenol is 2,6-di-t-butylphenol.

7. The process of claim 1 wherein the amount of the 2,6-dialkylphenol is about 0.15 to about 0.5 moles per 1 mole of the 4-alkylphenol.

8. The process of claim 1 wherein the amount of the bridging compound is about 0.8 to about 4 moles per 1 mole of the 4-alkylphenol and wherein the amount of the alkaline earth metal oxide or hydroxide is about 0.1 to about 4 moles per 1 mole of the 4-alkylphenol.

9. The process of claim 1 wherein the components (a) through (d) are reacted at about 150° C. to about 230° C. for about 2 to about 10 hours.

10. The process of claim 1 wherein the 4-alkylphenol is reacted with at least a portion of the alkaline earth metal oxide or hydroxide and at least a portion of the bridging agent prior to addition of the 2,6-dialkylphenol.

11. The process of claim 10 wherein, in a first step, about 0.1 to about 0.4 moles of calcium hydroxide and about 1 to about 3 moles of sulfur (as $S_1$), per mole of the 4-alkylphenol, are reacted with the 4-alkylphenol at about 170 to about 230° C. for about 3 to about 7 hours, and thereafter about 0.05 to about 0.5 moles of additional calcium hydroxide, about 0.25 to about 0.8 moles of additional sulfur, and about 0.15 to about 0.5 moles of the 2,6-dialkylphenol, per mole of the 4-alkylphenol, are added and reacted at about 150 to about 230° C. for about 1 to about 5 hours.

12. The process of claim 1 wherein the reaction is conducted in the presence of a solvent.

13. The process of claim 1 wherein the product of the reaction is subsequently treated with a molar excess of alkaline earth metal oxide or hydroxide and with carbon dioxide, thereby providing an overbased detergent.

14. The process of claim 1 wherein the product of the reaction is subjected to vacuum stripping.

15. The process of claim 1 wherein the amount of the 2,6-dialkylpheonl is about 0.15 to 1 mole per mole of the 4-alkylphenol.

16. The process of claim 15 wherein the bridging agent is sulfur.

* * * * *